(12) United States Patent
Benavitz et al.

(10) Patent No.: US 10,624,734 B2
(45) Date of Patent: Apr. 21, 2020

(54) SURGICAL ASSEMBLY FOR TISSUE REPAIR

(71) Applicant: Arthrex, Inc., Naples, FL (US)

(72) Inventors: William C. Benavitz, Naples, FL (US);
Donald K. Shuler, Naples, FL (US);
Stephen S. Burkhart, Boerne, TX (US); Maxwell C. Park, Calabasas, CA (US); Peter J. Millett, Vail, CO (US);
Tal S. David, San Diego, CA (US)

(73) Assignee: Arthrex, Inc., Naples, FL (US)

( * ) Notice: Subject to any disclaimer, the term of this patent is extended or adjusted under 35 U.S.C. 154(b) by 463 days.

(21) Appl. No.: 15/296,602

(22) Filed: Oct. 18, 2016

(65) Prior Publication Data

US 2018/0104045 A1 Apr. 19, 2018

(51) Int. Cl.
*A61B 17/58* (2006.01)
*A61F 2/08* (2006.01)
*A61B 17/04* (2006.01)

(52) U.S. Cl.
CPC ........ *A61F 2/0811* (2013.01); *A61B 17/0401* (2013.01); *A61B 2017/0403* (2013.01); *A61B 2017/044* (2013.01); *A61B 2017/0409* (2013.01); *A61B 2017/0412* (2013.01); *A61B 2017/0414* (2013.01); *A61F 2002/0829* (2013.01); *A61F 2002/0852* (2013.01); *A61F 2002/0858* (2013.01); *A61F 2002/0888* (2013.01)

(58) Field of Classification Search
CPC .............. A61B 2/0811; A61B 17/0401; A61B 17/0485; A61B 2017/0409; A61B 2017/0414; A61B 2017/0432; A61B 2017/042; A61B 2017/0422; A61B 2017/0424; A61B 2017/0425; A61B 2017/0427; A61B 2017/043; A61B 2017/0433; A61F 2002/0835; A61F 2002/0888; A61F 2002/0841; A61F 2002/0823; A61F 2002/0817
USPC .......... 606/300–321, 104, 99–100, 232–233, 606/228; 623/17.11–17.16; 81/52, 81/477–478, 427.5
See application file for complete search history.

(56) References Cited

U.S. PATENT DOCUMENTS 5,549,677 A * 8/1996 Durr .................... A61C 8/0018
411/397
5,632,748 A * 5/1997 Beck, Jr. ............... A61F 2/0811
606/232

(Continued)

*Primary Examiner* — Jessica Weiss
(74) *Attorney, Agent, or Firm* — Blank Rome LLP

(57) ABSTRACT

A method of tissue repair using a surgical assembly that includes the steps of assembling an implant and a driver, capturing tissue with the implant, installing the implant with the captured tissue in a socket or tunnel, advancing a tapered section of a set screw in the implant, thereby expanding the implant and fixing the implant with the captured tissue in the socket or tunnel, and releasing the driver from engagement with the set screw as the distal end of the set screw reaches the implant's closed end. A surgical assembly that includes an expandable implant having a hole with an entrance at a rear end of the implant and a closed end; a set screw, an implant insertion section, a driver engagement section, and a tapered section, where the implant insertion section is received in the hole of the implant, and a driver that is engaged with the set screw.

21 Claims, 10 Drawing Sheets

(56) References Cited

U.S. PATENT DOCUMENTS

| | | | |
|---|---|---|---|
| 6,361,258 B1* | 3/2002 | Heesch | F16B 23/0084 411/178 |
| 7,309,355 B2* | 12/2007 | Donnelly | A61F 2/0811 606/232 |
| 7,572,283 B1 | 4/2009 | Meridew | |
| 8,512,405 B2 | 8/2013 | Baird | |
| 8,523,902 B2 | 9/2013 | Heaven | |
| 8,790,368 B2 | 7/2014 | Sullivan | |
| 8,932,354 B2 | 1/2015 | Barwood | |
| 9,044,313 B2 | 6/2015 | Malcom | |
| 9,301,751 B2 | 4/2016 | Sullivan | |
| 10,034,742 B2* | 7/2018 | Diduch | A61B 17/8872 606/104 |
| 10,076,374 B2* | 9/2018 | Diduch | A61B 17/88 606/104 |
| 2004/0068262 A1 | 4/2004 | Lemos et al. | |
| 2004/0093031 A1 | 5/2004 | Burkhart et al. | |
| 2005/0216027 A1* | 9/2005 | Suh | A61B 17/8888 606/104 |
| 2007/0005077 A1* | 1/2007 | Null | A61B 17/862 606/104 |
| 2008/0161864 A1* | 7/2008 | Beck | A61F 2/0811 606/326 |
| 2009/0105718 A1* | 4/2009 | Zhang | A61B 17/8863 606/104 |
| 2009/0275954 A1* | 11/2009 | Phan | A61B 17/7064 606/104 |
| 2009/0312794 A1* | 12/2009 | Nason | A61B 17/0401 606/232 |
| 2010/0137917 A1* | 6/2010 | Koogle, Jr. | A61F 2/0811 606/300 |
| 2010/0145395 A1* | 6/2010 | Graf | A61F 2/0811 606/304 |
| 2010/0185246 A1* | 7/2010 | Castaneda | A61B 17/8875 606/305 |
| 2011/0022053 A1* | 1/2011 | Schlueter | A61F 2/389 606/100 |
| 2011/0071579 A1* | 3/2011 | Reach, Jr. | A61B 17/0401 606/327 |
| 2011/0106252 A1* | 5/2011 | Barwood | A61F 2/0811 623/13.14 |
| 2012/0197311 A1* | 8/2012 | Kirschman | A61B 17/7064 606/304 |
| 2013/0103054 A1* | 4/2013 | Housman | A61B 17/0401 606/139 |
| 2014/0249579 A1 | 9/2014 | Heaven | |
| 2014/0288567 A1* | 9/2014 | Kroll | A61B 17/8886 606/104 |
| 2015/0190130 A1* | 7/2015 | Groh | A61B 17/0401 606/232 |
| 2015/0335418 A1 | 11/2015 | Heaven | |
| 2016/0030159 A1 | 2/2016 | Ticker | |
| 2016/0113644 A1* | 4/2016 | Diduch | A61B 17/88 606/104 |
| 2016/0113757 A1* | 4/2016 | Diduch | A61B 17/8872 606/104 |
| 2016/0113758 A1* | 4/2016 | Diduch | A61F 2/0811 606/232 |
| 2016/0143672 A1* | 5/2016 | Black | F16B 25/001 29/283 |
| 2016/0310260 A1* | 10/2016 | Sengun | A61B 17/0401 606/327 |

* cited by examiner

SURGICAL ASSEMBLY FOR TISSUE REPAIR

FIELD OF THE INVENTION

The present application relates to the field of surgery and, more particularly, to a method and apparatus for improved soft tissue repair or reconstruction, including but not limited to tenodesis fixation.

BACKGROUND OF THE INVENTION

When soft tissue, such as a tendon or ligament, becomes detached from a bone, surgery is often required to reattach or reconstruct the tissue.

When tendon tissue requires fixation, this can be referred to as a tenodesis repair. An example of such a repair involves the long head biceps tendon. Other soft tissue can be used for repair or reconstruction purposes, in a similar manner as tenodesis repair, when soft tissue is fixated within a bony tunnel or socket. Soft tissue includes, but is not limited to, grafts that are synthetic or natural. Conventional techniques for soft tissue repair or reconstruction in this setting can result in failure to properly anchor the soft tissue to bone and/or damage to the soft tissue itself.

Therefore, a need exists for an improved soft tissue repair or reconstruction method, including tenodesis, and surgical apparatus for conducting the same that ensures the tendon or other relevant soft tissue is properly anchored and not damaged.

SUMMARY OF THE INVENTION

Accordingly, an exemplary embodiment of the present invention provides a method of tissue repair or reconstruction, comprising the steps of assembling an implant and a driver, the implant having a hole with an entrance at a rear end of the implant and a closed end opposite the entrance, by the steps of inserting a distal end of a set screw into the entrance of the hole of the implant until an implant insert section of the set screw is received in the hole with a driver engagement section near a proximal end of the set screw and a tapered section, between the implant insert and driver engagement sections, remaining outside of the implant, and engaging a distal end of the driver with the driver engagement section of the set screw; capturing tissue with the implant; installing the implant with the captured tissue in a tunnel or socket, such as a bone tunnel or bone socket; advancing the tapered section of the set screw in the hole of the implant, thereby expanding the implant and fixing the implant with the captured tissue in the tunnel or socket, such as a bone tunnel or bone socket; and releasing the driver from engagement with the set screw when the set screw is substantially inserted into the hole of the implant. In one embodiment, the driver is released from engagement with the set screw substantially simultaneously with the distal end of the set screw reaching the closed end of the hole of the implant.

The present invention may also provide a method of tissue repair or reconstruction, comprising the steps of assembling an implant and a driver, the implant having a hole with an entrance at a rear end of the implant and a closed end opposite the entrance, and the driver having inner and outer shafts, by the steps of inserting a distal end of a set screw into the entrance of the hole of the implant until an implant insert section of the set screw is received in the hole with a driver engagement section near a proximal end of the set screw and a tapered section, between the implant insert and driver engagement sections, remaining outside of the implant, engaging the outer shaft of the driver at the distal end of the driver with the driver engagement section of the set screw, and coupling the inner shaft of the driver at the distal end of the driver with a proximal end of the set screw; capturing tissue with the implant; installing the implant with the captured tissue in a tunnel or socket, such as a bone tunnel or bone socket; coupling an actuating member with the inner shaft of the driver at a proximal end of the driver; and rotating the actuating member to advance the tapered set screw into the hole of the implant, thereby expanding the implant and fixing the implant with the captured tissue in the tunnel or socket as the case may dictate.

The present invention may further provide a surgical assembly for tissue repair, comprising an expandable implant having a hole with an entrance at a rear end of the implant and a closed end opposite the entrance; a set screw having distal and proximal ends, an implant insertion section near the distal end, a driver engagement section near the proximal end, and a tapered section between the implant insertion and driver engagement sections, at least the implant insertion section being received in the hole of the implant, the proximal end including inner and outer couplings; and a driver having a distal end engaged with both of the inner and outer couplings of the set screw.

Other objects, advantages and salient features of the invention will become apparent from the following detailed description, which, taken in conjunction with the annexed drawings, discloses a preferred embodiment of the present invention.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE EXEMPLARY EMBODIMENTS

Referring to FIGS. 1-14, the present invention generally relates to a method of tissue repair, such as a tenodesis repair or fixation, using a surgical assembly 10 that may include a push-in type implant 100 and associated driver 102. The method and surgical assembly 10 of the present invention are designed to maximize efficiency of the repair while preventing over insertion of the implant 100 in bone, providing a more secure anchoring of the implant 100 in bone by limiting the spreading of the tissue around the implant 100, and limiting damage to the tissue during the repair. The method and surgical assembly 10 of the present invention is also designed to allow substantially simultaneous release of driver 102 when the repair is complete.

Figure 1:
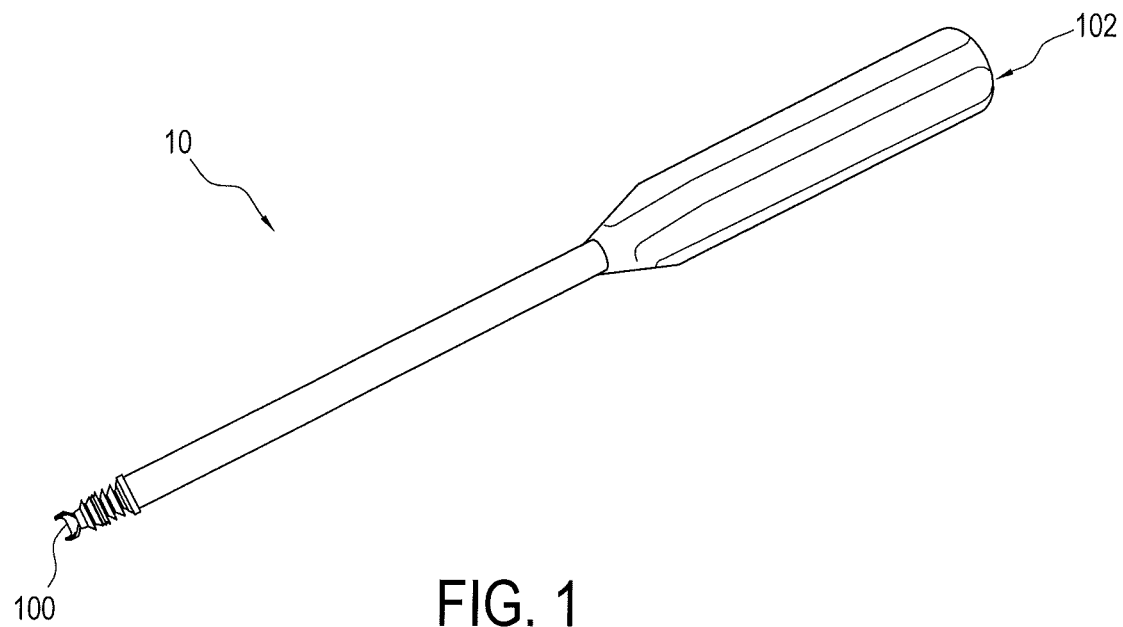
FIG. 1 is a perspective view of a drive and implant assembly used in accordance with an exemplary method of the present invention.
Figure 2:
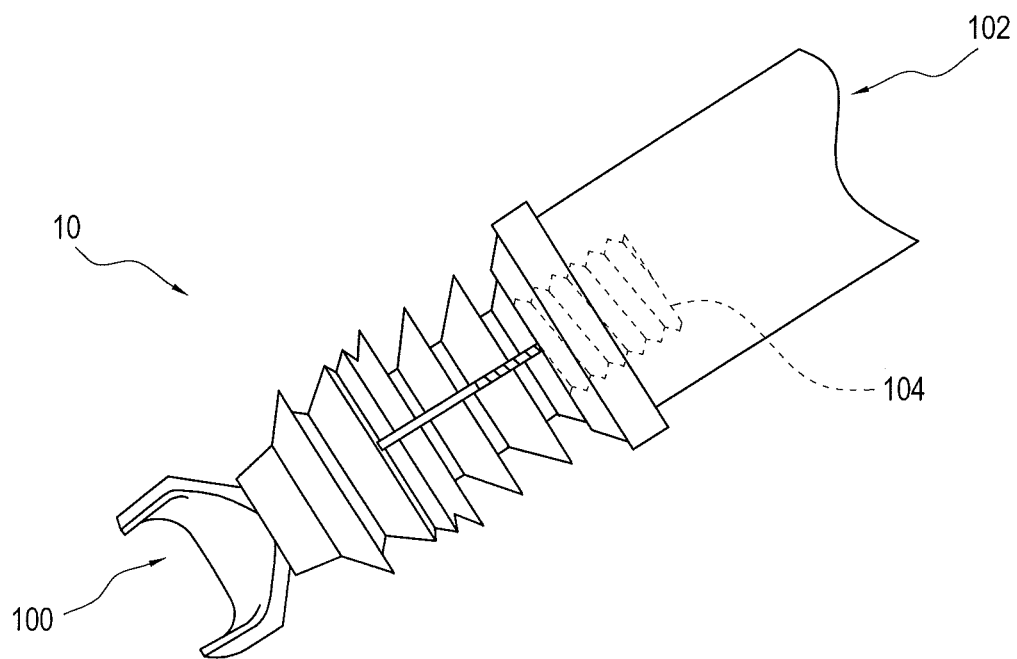
FIG. 2 is an enlarged partial view of the drive and implant assembly illustrated in FIG. 1.
Figure 3:
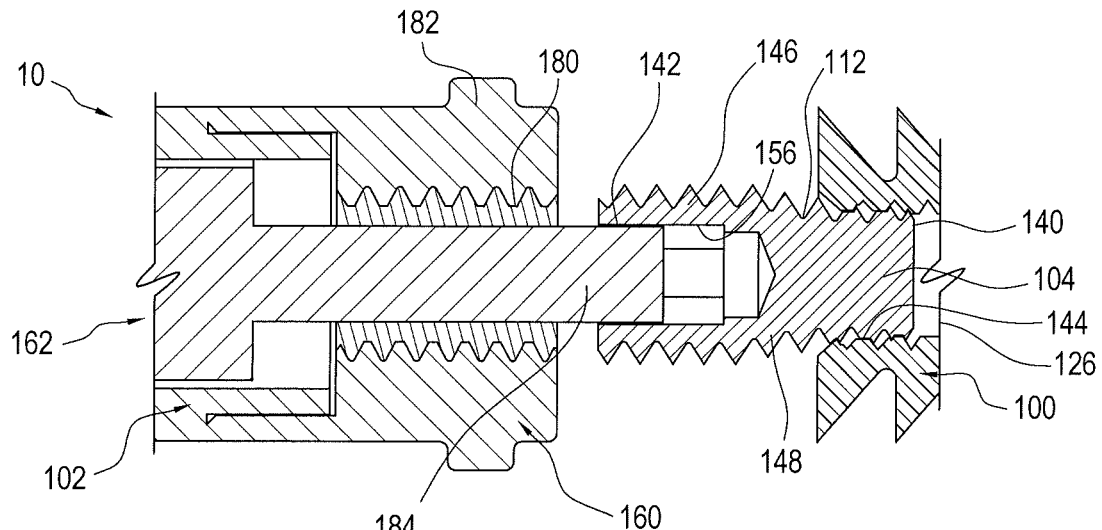
FIG. 3 is an exploded cross-sectional view of the driver and implant assembly illustrated in FIG. 1

FIGS. 1-3 illustrate an exemplary embodiment of the surgical assembly 10 including implant 100 and driver 102 coupled together by a set screw 104. Using an actuating member 200 (FIG. 7), driver 102 advances set screw 104 into implant 100 to secure the same in a socket or tunnel formed in bone or formed in a bone compatible material which may be natural or synthetic, at least partially porous, and that preferably does not impede attachment of tissue thereto. A front end 110 of implant 100 is configured for insertion into the socket or tunnel and its rear end 112 is connected to the driver 102. In a preferred embodiment, front end 110 of implant 100 includes a saddle 114 to facilitate capture of the tissue, such as a tendon or graft. Saddle 114 may be either separate from and attached to the body 116 of the implant 100 or formed as one piece with body 116. Saddle 114 may be, for example, a generally forked end (FIG. 4A), alternatively a closed eyelet 114' (FIG. 4D), or a combination (FIG. 4E). Saddle and eyelet embodiments may be produced in multiple forms. For example, the forked embodiment of saddle 114 may include a single or multiple eyelets 115 (FIG. 4E). Further, the implant body 120 itself could embody an eyelet 117 at its front end (FIG. 4E). The eyelets may be used for containing standard suture or tape-type suture; such sutures can be used for additional soft tissue fixation purposes in order to enhance failure loads.

Figure 4A:
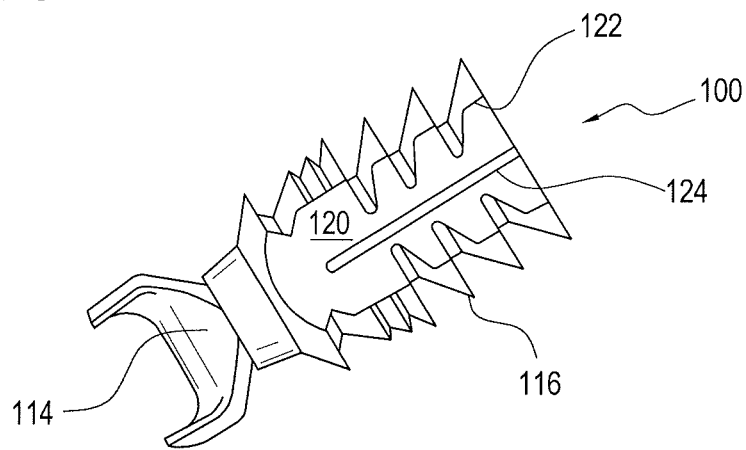
FIGS. 4A-4E are various views of an implant of the driver and implant assembly illustrated in FIG. 1.
Figure 4B:
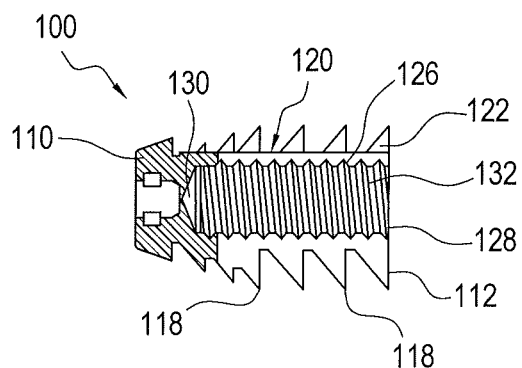
Figure 4C:
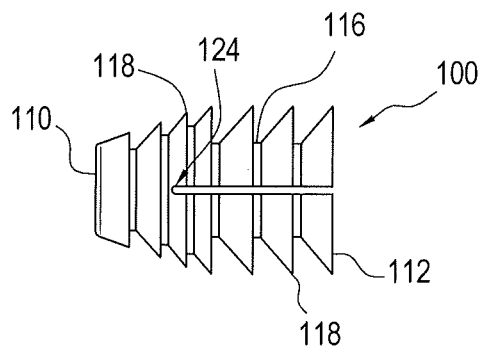
Figure 4D:
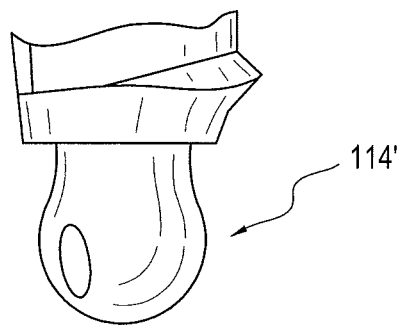
Figure 4E:
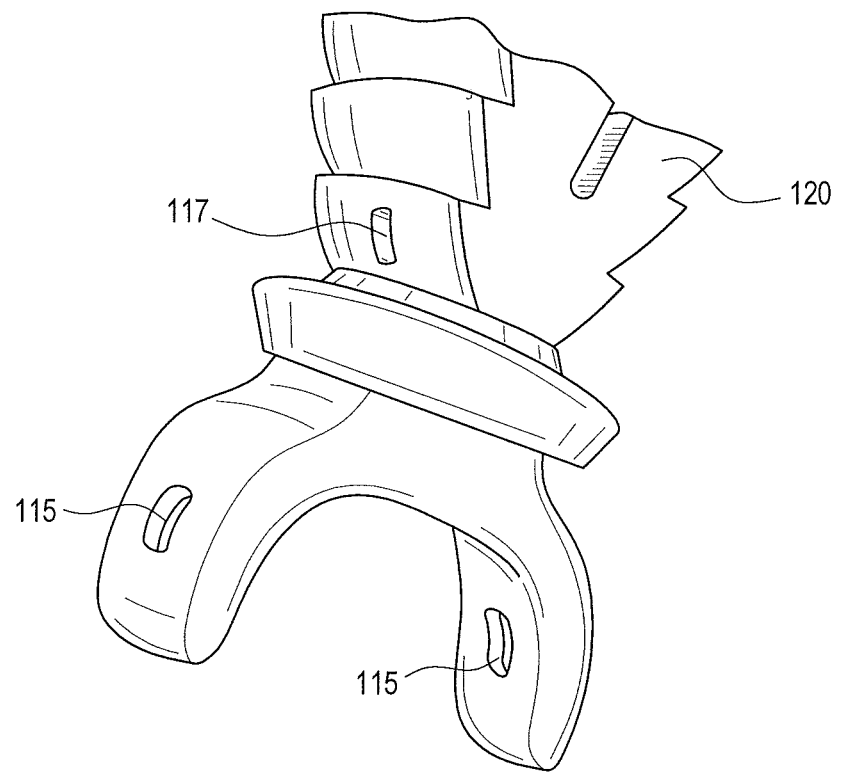

As seen in FIGS. 4A-4C, implant 100 includes a plurality of radial barbs 118 extending outwardly from body 116. Radial barbs 118 are designed to grip the bone when the implant is installed in the socket or tunnel. Although it is preferred that radial barbs 118 extend generally the length of implant body 116, fewer radial barbs 118 may be provided that extend from different locations of implant body 116. At an outer side of body 116, a substantially flat tissue engagement surface 120 is provided, as best seen in FIGS. 4A and 4B. Thus radial barbs 118 may extend around body 116 of implant 100 except at tissue engagement surface 120. The substantially flat tissue engagement surface 120 is configured to allow the tissue to slide along implant body 116 as implant 100 is being installed in the socket or tunnel, thereby reducing potential damage to the tissue during the repair. Radial barbs 118 terminate at ends 122 at the tissue engagement surface 120. These ends 122 together with tissue engagement surface 120 form a generally U-shaped area for containing the tissue to prevent the tissue from radially spreading around implant 100 allowing more surface area of implant 100 to contact directly with the cortical bone, thereby increasing pull-out resistance. A longitudinal slot 124 is preferably provided in implant body 116 at tissue engagement surface 120 to allow implant 100 to expand inside of the socket or tunnel. Longitudinal slot 124 may be located anywhere on body 116 as long as implant 100 can be expanded. And more than one longitudinal slot may be provided in implant body 116.

Internal to implant body 116 is a tapped hole 126 that receives the set screw 104 and engages driver 102. The entrance 128 to the hole 126 is located at the rear end 112 of implant 100. Hole 126 includes a closed end 130 opposite the entrance 128. Hole 126 has an inner diameter 132 that is preferably threaded for engaging the threads of set screw 104.

Figure 5A:
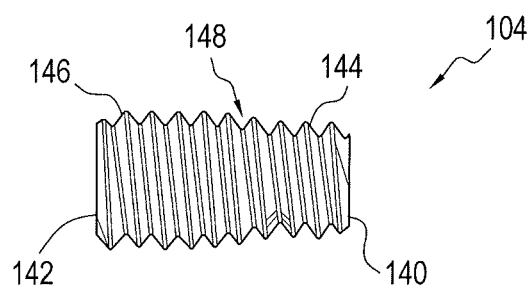
FIGS. 5A-5D are various views of a set screw of the drive and implant assembly illustrated in FIG. 1.
Figure 5B:
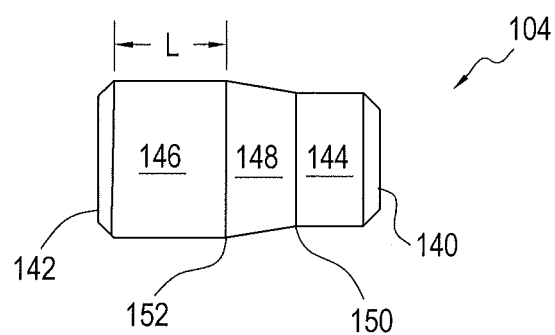
Figure 5C:
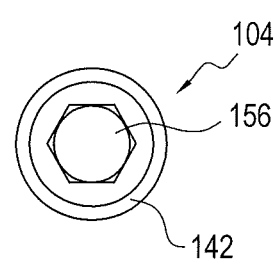
Figure 5D:
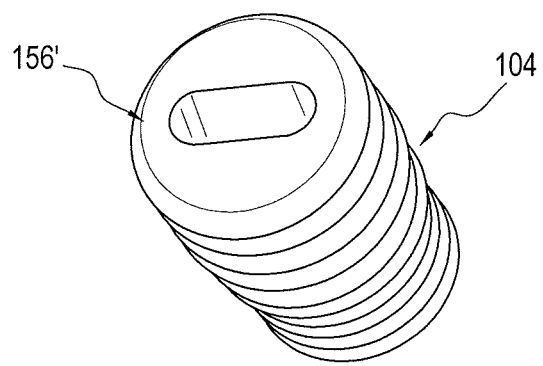

As seen in FIGS. 5A-5C, the set screw 104 includes a distal end 140, an opposite proximal end 142, an implant insertion section 144 near distal end 140, a driver engagement section 146 near proximal end 140, and a tapered section 148 between implant insertion and driver engagement sections 144 and 146. Set screw 104 is preferably formed of PEEK, titanium, or the like. As seen in FIG. 5B, which illustrates set screw 104 without its threads for clarity, tapered section 148 tapers inwardly from driver engagement section 146 to implant insertion section 144 such that the minor diameter 150 of tapered section 148 is substantially the same as the diameter of implant insert section 144 and the major diameter 152 of tapered section 148 is substantially the same as the diameter of driver engagement section 146. A length L of driver engagement section 146 is preferably longer than the lengths of each of the other sections 144 and 148. The diameter of driver engagement section 146 may be substantially equal to an inner diameter of driver 102 and the diameter of implant insert section 144 may be substantially equal to the inner diameter 132 of hole 126 of implant 100. Driver engagement section 146 of set screw 104 defines an outer coupling for engaging driver 102. An inner coupling 156 is also provided at the proximal end 142 of the set screw for engaging the driver. The inner coupling 156 may be, for example, a substantially hexagonal shaped socket (FIG. 5C) or a substantially rectangular shaped socket 156' (FIG. 5D), and the like, configured to receive a corresponding component of driver 102 that opens at proximal end 142 and extends into driver engagement section 146, as best seen in FIGS. 3 and 5C.

Figure 6A:
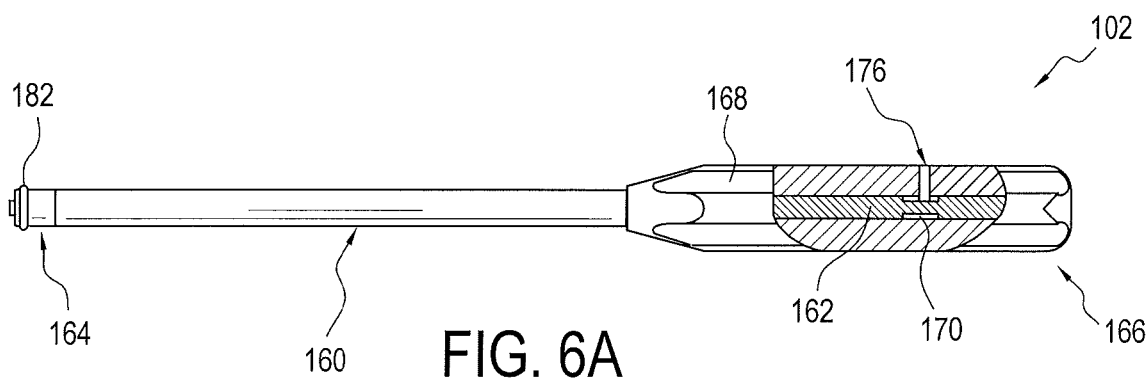
FIGS. 6A-6E are various views a driver and its components of the driver and implant assembly illustrated in FIG. 1.
Figure 6B:
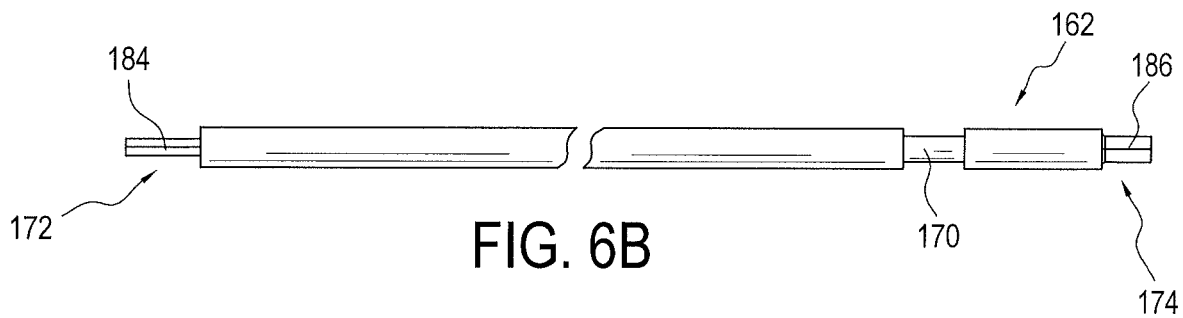
Figure 6C:
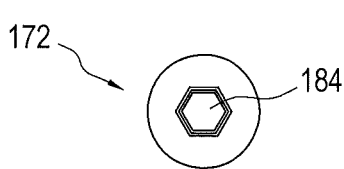
Figure 6D:
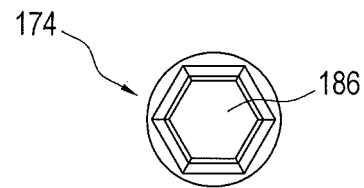
Figure 6E:
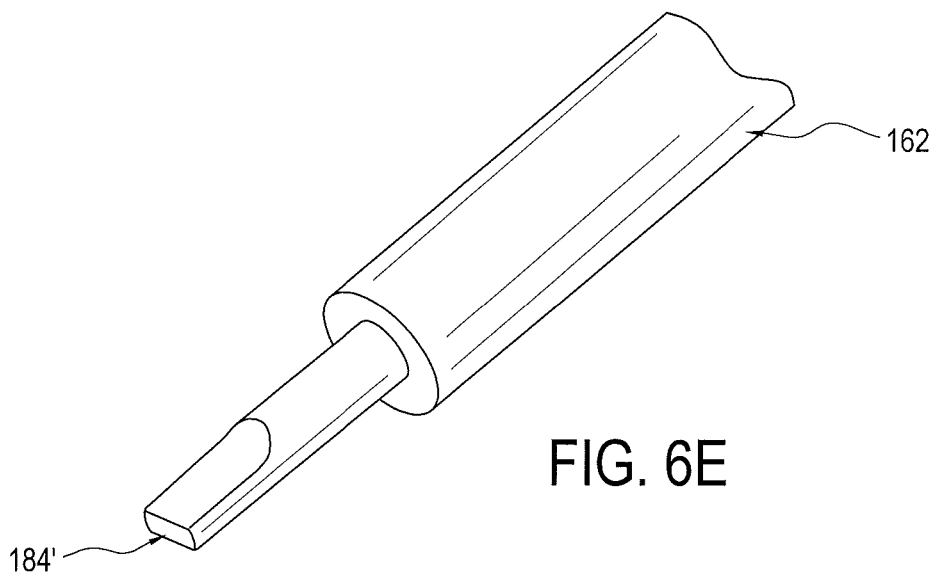

As seen in FIGS. 6A to 6D, driver 102 includes an outer shaft 160 that receives an inner shaft 162. Outer shaft 160 includes a distal end 164 and an opposite proximate end 166 with outer shaft 160 being open at both ends 164 and 166. Proximate end 166 of outer shaft 160 may include a gripping portion 168. Inner shaft 162 is axially moveable with respect to outer shaft 160 for a controlled distance. That controlled distance is defined by the length of an outer annular recess 170 disposed around a portion of inner shaft 162. Outer annular recess 170 may be located anywhere on inner shaft 162 but is preferably disposed closer to the inner shaft's proximal end 174 than its opposite distal end 172. A pin 176 may be used to couple outer and inner shafts 162 and 164 while allowing inner shaft 162 to move axially with respect to outer shaft 160 for the controlled distance. As best seen in FIG. 6A, pin 176 preferably extends through outer shaft 160 at its gripping portion 168 such that its end is received in the outer annular recess 170 of inner shaft 162. As such, pin 176 captures inner shaft 162 from falling out of outer shaft 160 and restricts the amount of forward travel of inner shaft 162 which restricts the amount of insertion depth of the set screw 104 within the implant 100.

At the distal end 164 of the outer shaft 160 is an inner engagement 180 for engaging set screw 104, as best seen in FIG. 3. The inner engagement 180 is preferably internal threads configured to engage the threads of driver engagement section 146 of set screw 104. The length L (FIG. 5B) of driver engagement section 146 of set screw 104 is preferably selected to correspond to the length and number of internal threads 180 of outer shaft 160, such that outer shaft 160 is released from engagement with set screw 104, when set screw 104 is fully received in hole 126 of implant 100. An outer stopping ring 182 may be provided at the distal end 164 of outer shaft 160, as best seen in FIGS. 3 and 6A, to prevent over insertion of implant 100 into bone during the repair.

At the distal end 172 of inner shaft 162 is a set screw coupling 184 configured to engage set screw 104. Set screw coupling 184 may be, for example, a substantially hexagonally shaped end (FIG. 6C) or a substantially rectangular shaped end 184' (FIG. 6E), and the like, designed for insertion into the corresponding socket 156 or socket 156' at the proximal end 142 of set screw 104.

Figure 7:
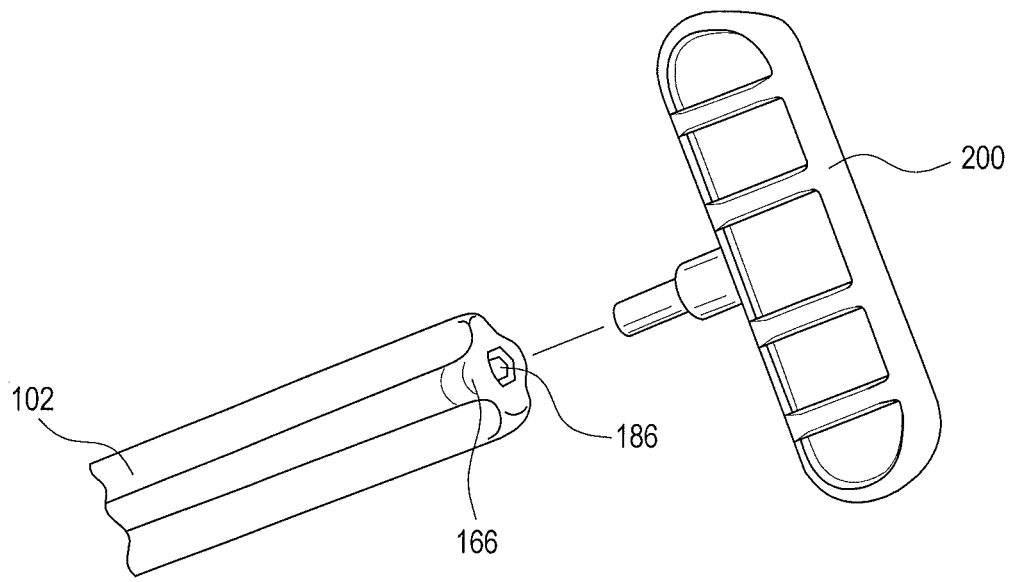
FIG. 7 is an exploded perspective view of an actuating member used with the driver and implant assembly illustrated in FIG. 1.
Figure 8A:
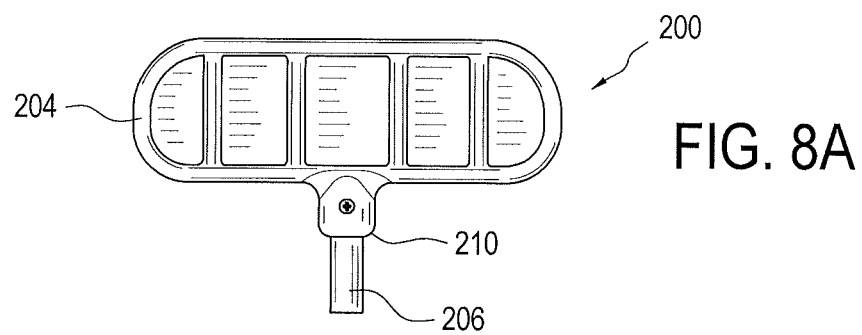
FIGS. 8A-8C are various views of the actuating member illustrated in FIG. 7.
Figure 8B:
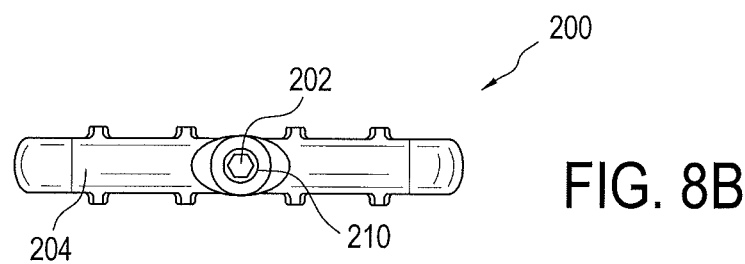
Figure 8C:
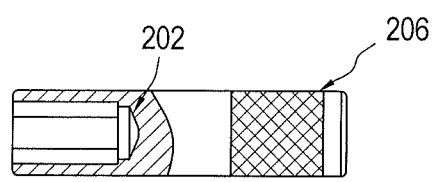

The proximal end 174 of inner shaft 162 engages with the actuating member 200, as seen in FIG. 7. The proximal end 174 of inner shaft 162 includes a coupling 186 for engaging a corresponding shaft coupling 202 of actuating member 200. Actuating member 200 may include a handle 204 and leg portion 206 extending therefrom, as seen in FIG. 8A. The shaft coupling 202 may be located in the leg portion 206. The outer diameter of leg portion 206 is sized such that is receivable in the open proximal end 166 of outer shaft 160. Coupling 186 at the proximal end 174 of the driver's inner shaft 162 may be, for example, a substantially hexagonal shaped end (FIG. 6B), a substantially rectangular shaped end, and the like; and shaft coupling 202 of actuating member 200 may be, for example, a substantially hexagonal shaped socket (FIG. 8C), or a substantially rectangular shaped socket, and the like, that is sized to receive and engage the coupling 186 or inner shaft 162. A stopping shoulder 210 may be provided on leg portion 206. The location of stopping shoulder 210 on leg portion 206 may be selected such that stopping shoulder 210 abuts the proximal end 166 of the driver's outer shaft 160 when advancing set screw 104 in implant 100 via the driver's inner shaft 162. This prevents over insertion or countersinking of set screw 104 into implant 100.

An exemplary method of tissue repair of the present invention may include the steps of inserting the distal end 140 and implant insertion section 144 of set screw 104 into hole 126 at the rear end 112 of implant 100. Set screw 104 is preferably initially inserted into the implant's hole 126 up to where tapered section 148 of set screw 104 begins, that is at tapered section's minor diameter 150. The exposed portion of set screw 104 now protruding from rear end 112 of implant 100, that is driver engagement section 146 and tapered section 148, may be measured to assure a consistent number of turns of actuating member 200 to release set screw 104 from the inner shaft 162 of driver 102.

Driver 102 is then coupled to the exposed portion of set screw 104. More specifically, the inner engagement 180 of outer shaft 160 of driver 102 is engaged with driver engagement section of set screw 104. In addition, set screw coupling 184 or 184' of inner shaft 162 of driver 102 is inserted into socket 156 or 156' at the proximal end 142 of set screw 104.

Implant 100 may then be installed in the socket or tunnel, such as a bone socket or bone tunnel. The socket or tunnel preferably has a diameter that is substantially equal to a major diameter, that is the largest diameter, of implant body 116. The tissue, such as a tendon, is centered over the socket or tunnel with a substantial portion of the tendon proximal to the socket or tunnel. The implant saddle 114 is then positioned over the tendon or other soft tissue, and preferably in-line with the fibers of the tendon or other soft tissue, and in-line with the entrance 128 of the hole 126 of the implant body 116. Implant 100 may then be installed in the socket or tunnel by mallet strikes, for example, to the proximal end 166 of the driver 102, until the stopping ring 182 of the driver's outer shaft 160 abuts the cortical surface of the bone. This assures that the rear end 112 of the implant 100 is generally flush with or a maximum of 1 mm recessed into the cortical surface of the bone.

Actuating member 200 is then coupled to driver 102. In particular, leg portion 206 of actuating member 200 is inserted into the open proximal end 166 of the driver's outer shaft 160 such that its shaft coupling or socket 202 engages the coupling 186 at the proximal end 174 of the driver's inner shaft 162. Then rotating actuating member 200 in a clockwise manner advances set screw 104 implant 100 because of the engagement between the set screw coupling 184 or 184' of the driver's inner shaft 162 and the socket 156 or 156' of set screw 104. As the set screw is advanced by rotating actuating member 200, tapered section 148 of set screw 104 enters hole 126 of implant 100, thereby expanding the implant 100 to form a press fit with the socket or tunnel.

When set screw 104 reaches full insertion into implant 100, that is driver engagement section 146 of set screw 104 is received in the implant's hole 126, the stopping shoulder 210 on the leg portion 206 of actuating member 200 will contact the proximal end 166 of driver 102 to prevent set screw 104 and implant 100 from being countersunk. After substantial insertion of set screw 104 into implant 100, driver 102, and particularly the distal end 164 of its outer shaft 160, is released from engagement with the implant 100. In one embodiment, the driver 102 is released from implant 100 substantially simultaneously with full insertion of set screw 104 into implant 100.

Figure 9:
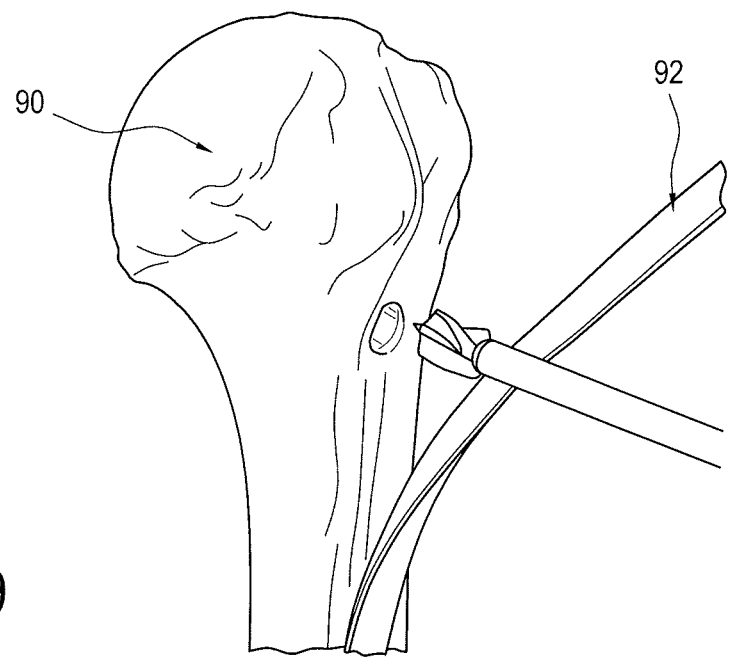
FIGS. 9-14 illustrates steps in accordance with an exemplary method of the present invention using the driver and implant assembly illustrated in FIG. 1.
Figure 10:
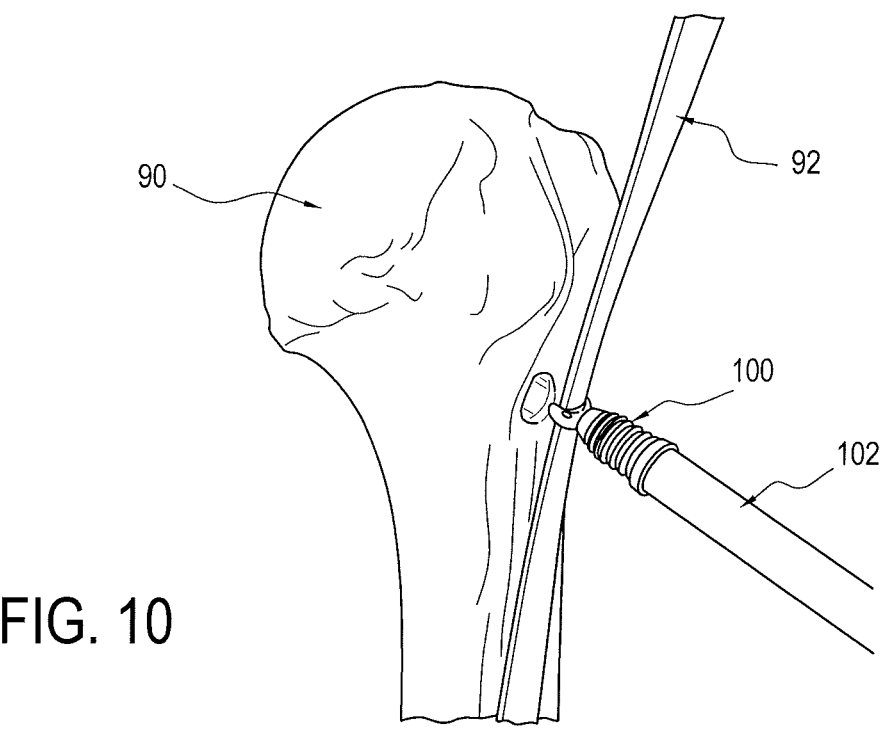
Figure 11:
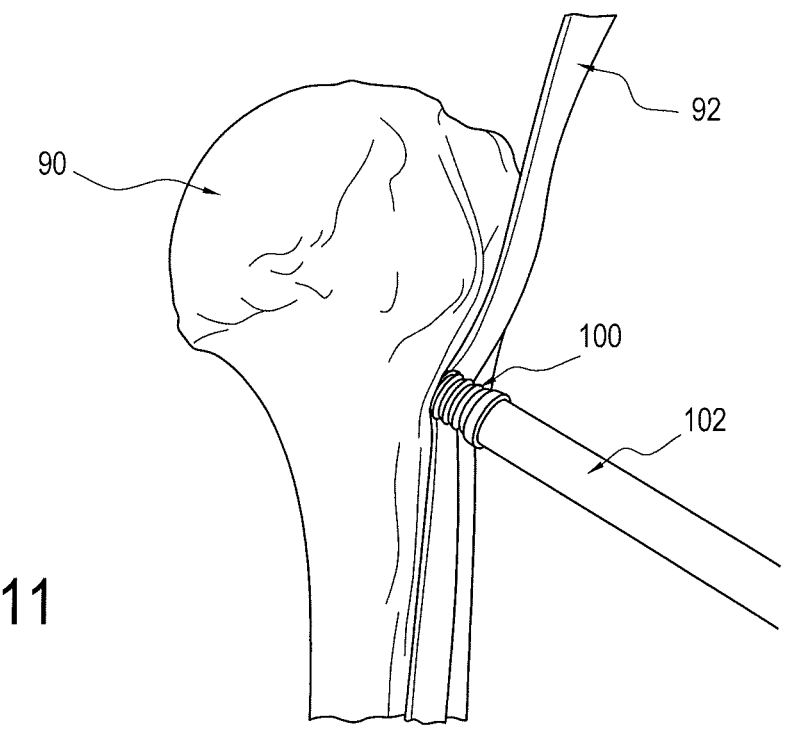
Figure 12:
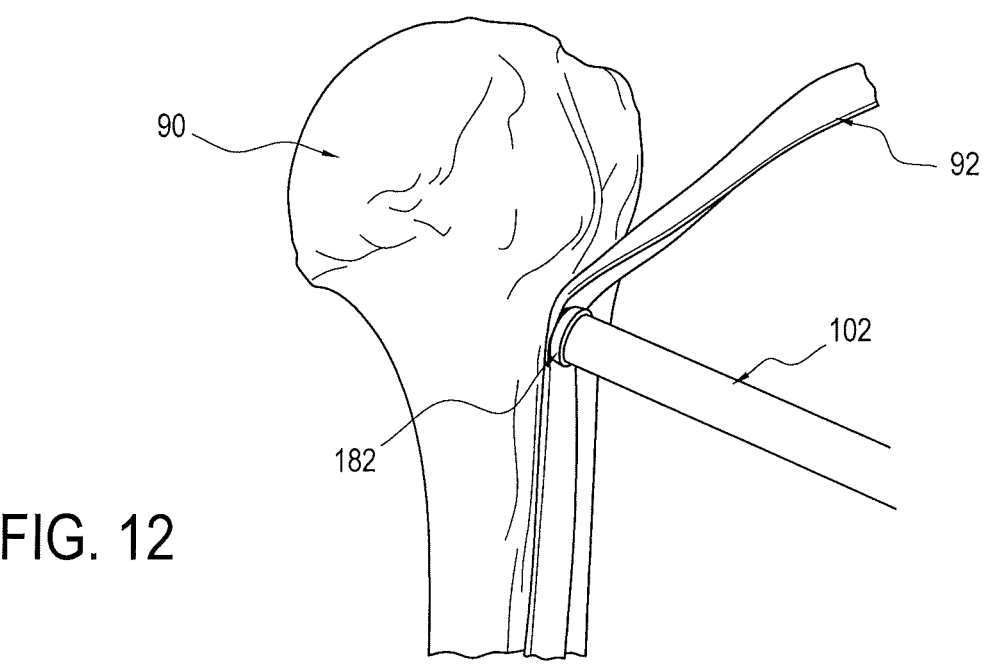
Figure 13:
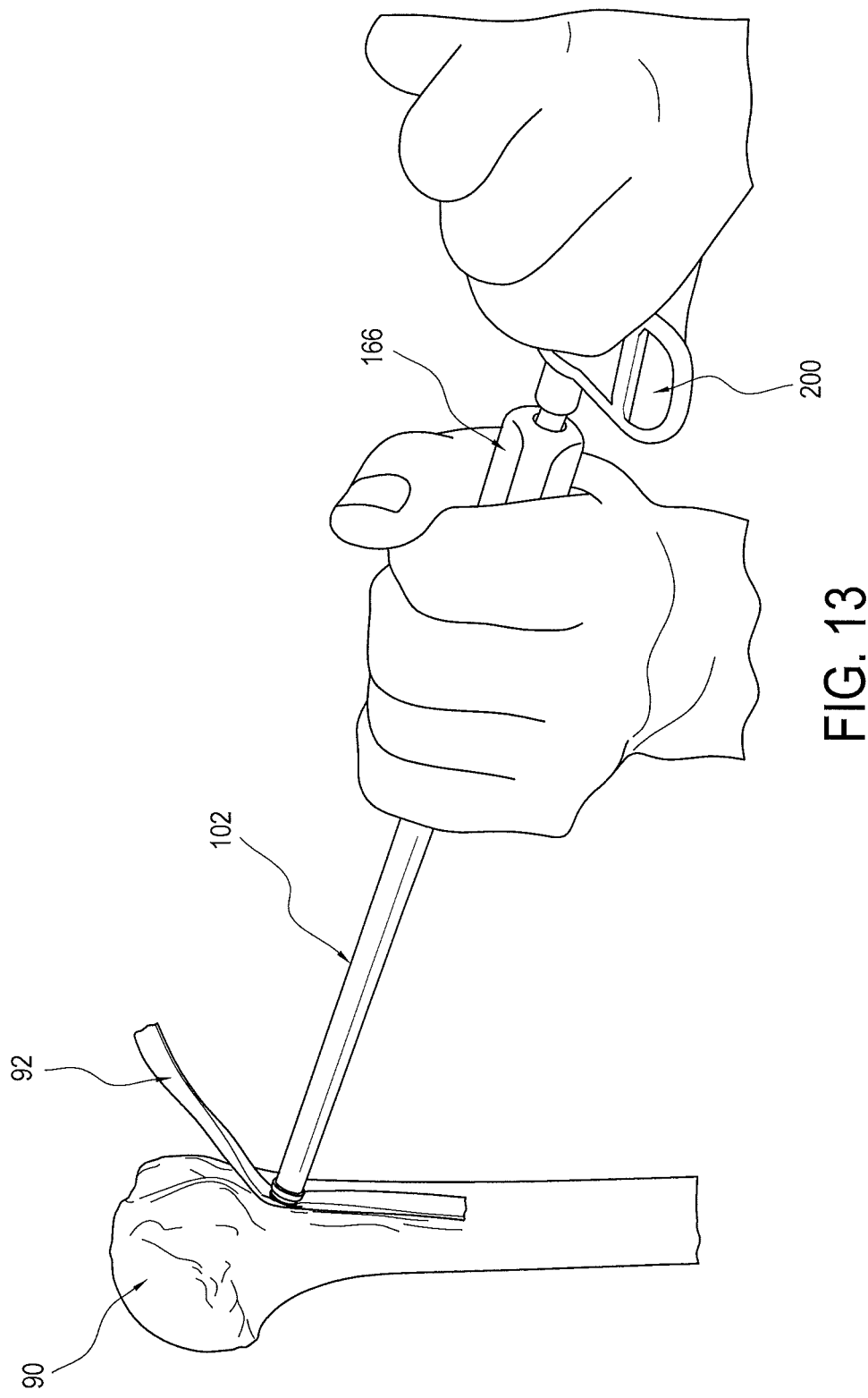
Figure 14:
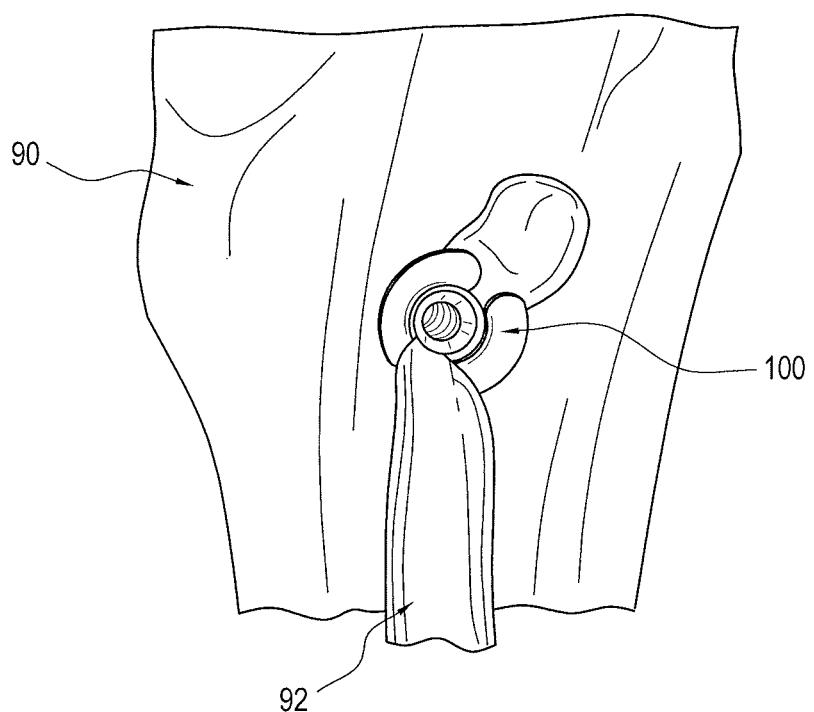

FIGS. 9 thru 14 illustrate the steps of an exemplary method of the present invention using the driver and implant assembly. FIG. 9 shows an initial step of forming a socket or tunnel in the bone 90, such as in the proximal humerus, using a conventional tool, such as a pilot headed reamer. FIG. 10 illustrates a next step of capturing the tissue 92, such as the biceps tendon, in the saddle 114 of the implant 100 and positioning the same over the socket or tunnel of the bone 90. Once the tissue 92 is properly positioned over the socket or tunnel, the tissue 92 is then pushed into the socket or tunnel with the saddle 114 until resistance is met with the body of the implant 100, as seen in FIG. 11. Proximal end 166 (FIG. 13) of the driver 102 is then progressively impacted with a surgical mallet until the stopping ring 182 of the driver meets the bone's surface, thereby preventing implant 100 from being inserted any further into the socket or tunnel of the bone 90, as seen in FIG. 12. Actuating member 200 is then inserted into proximal end 166 of driver 102 and rotated (such as in a clockwise direction), as seen FIG. 13, inserting the set screw 104 (FIG. 3), which expands implant 100 until driver 102 automatically releases, as described above. FIG. 14 shows the driver removed and the implant 100 fully installed and expanded to secure the tissue in the socket or tunnel.

While particular embodiments have been chosen to illustrate the invention, it will be understood by those skilled in the art that various changes and modifications can be made therein without departing from the scope of the invention as defined in the appended claims. For example, the engaging components of a substantially hexagonal or rectangular shaped socket and a substantially hexagonal or rectangular shaped end may be reversed. That is the inner coupling 156 or 156' of set screw 104 may be a substantially hexagonally or rectangular shaped end and the set screw coupling 184 or 184' of the driver's inner shaft 162 may be a corresponding substantially hexagonally or rectangular shaped socket and vice versa. Likewise, the coupling 186 of the driver's inner shaft may be a substantially hexagonal or rectangular shaped socket and the coupling 202 of actuating member 200 may a substantially hexagonal or rectangular shaped end that is inserted into coupling 186 and vice versa.

What is claimed is:

1. A surgical assembly, comprising:
   an expandable implant having a front end comprising a saddle configured to capture tissue therein, and an opposite rear end having a hole with an entrance at the rear end and a closed end opposite the entrance;
   a set screw having distal and proximal ends, an implant insertion section near the distal end, a driver engagement section near the proximal end, and a tapered section between the implant insertion section and the driver engagement section, at least the implant insertion section being insertable in the hole of the expandable implant, and wherein the proximal end comprises inner and outer couplings;
   a driver comprising inner and outer shafts,
   wherein a distal end of the outer shaft is engageable with the outer coupling of the set screw and a distal end of the inner shaft is engageable with the inner coupling of the set screw,
   and
   an actuating member configured to be coupled to a proximal end of the inner shaft of the driver, the actuating member comprising a handle, a leg member extending from the handle, and a stopping shoulder extending around the leg member.

2. The surgical assembly of claim 1, wherein an outer diameter of the driver engagement section of the set screw is substantially equal to an inner diameter of the distal end of the outer shaft of the driver, an outer diameter of the implant insertion section of the set screw is substantially equal to an inner diameter of the hole of the expandable implant, and wherein the tapered section tapers inwardly from the driver engagement section to the implant insertion section.

3. The surgical assembly of claim 2, wherein a length of the driver engagement section is larger than a length of the implant insertion section and a length of the tapered section.

4. The surgical assembly of claim 1, wherein the outer coupling comprises threads configured to engage inner threads of the outer shaft, and the inner coupling includes a socket configured to receive the distal end of the inner shaft.

5. The surgical assembly of claim 1, wherein a pin couples the inner and outer shafts of the driver.

6. The surgical assembly of claim 5, wherein the pin extends through the outer shaft and is received in an outer annular recess of the inner shaft.

7. The surgical assembly of claim 1, wherein the expandable implant comprises a body having radial barbs extending outwardly therefrom.

8. The surgical assembly of claim 7, wherein the body of the expandable implant comprises a substantially flat tissue engagement surface on at least one side thereof, wherein the substantially flat tissue engagement surface is devoid of any outwardly extending members and allows tissue to slide along the expandable implant as the expandable implant is installed into a socket or tunnel.

9. The surgical assembly according to claim 8, wherein the substantially flat tissue engagement surface includes a longitudinal slot that is configured to allow the expandable implant to expand.

10. The surgical assembly of claim 8, wherein the socket or tunnel is a bone socket or bone tunnel.

11. The surgical assembly of claim 1, wherein the hole of the expandable implant is threaded.

12. The surgical assembly of claim 1, wherein the saddle comprises at least one of a forked end or a closed eyelet.

13. The surgical assembly of claim 1, wherein a length of the driver engagement section of the set screw corresponds to a length of an inner engagement at the distal end of the outer shaft.

14. The surgical assembly of claim 13, wherein the inner engagement of the outer shaft comprises an internal thread.

15. The surgical assembly of claim 1, wherein the inner shaft of the driver is axially movable with respect to the outer shaft of the driver.

16. A surgical assembly, comprising:
    an expandable implant having a front end configured to capture tissue therein and an opposite rear end having a hole with an entrance at the rear end and a closed end opposite the entrance;
    a set screw having distal and proximal ends, an implant insertion section near the distal end, a driver engagement section near the proximal end, and a tapered section between the implant insertion section and the driver engagement section, at least the implant insertion section being insertable in the hole of the expandable implant, wherein the proximal end comprises inner and outer couplings;
    a driver comprising inner and outer shafts, the inner shaft being axially moveable within the outer shaft, the outer shaft having a radially inwardly facing engagement at a distal end thereof, wherein a distal end of the inner shaft is engageable with the inner coupling of the set screw, and wherein the outer coupling of the set screw is insertable into the distal end of the outer shaft to engage the radially inwardly facing engagement of the outer shaft of the driver;
    and
    an actuating member configured to be coupled to a proximal end of the inner shaft of the driver, the actuating member comprising a handle, a leg member extending from the handle, and a stopping shoulder extending around the leg member.

17. The surgical assembly of claim 16, wherein the inner shaft is axially movable with respect to the outer shaft by a controlled distance.

18. The surgical assembly of claim 17, wherein the controlled distance is defined by an outer annular recess of the inner shaft.

19. The surgical assembly of claim 18, wherein a pin extends through the outer shaft and is received in the outer annular recess of the inner shaft, thereby coupling the inner and outer shafts.

20. The surgical assembly of claim 16, wherein the front end of the expandable implant comprises at least one of a forked end or a closed eyelet for capturing the tissue.

21. A surgical assembly, comprising:
    an expandable implant having a hole with an entrance at a rear end of the expandable implant and a closed end opposite the entrance;
    a set screw having distal and proximal ends, an implant insertion section near the distal end, a driver engagement section near the proximal end, and a tapered section between the implant insertion section and the driver engagement section, at least the implant insertion section being insertable in the hole of the expandable implant, wherein the proximal end comprises inner and outer couplings;
    a driver having a distal end engageable with both of the inner and outer couplings of the set screw, the driver comprising inner and outer shafts, the outer shaft being engageable with the outer coupling of the set screw and the inner shaft being engageable with the inner coupling of the set screw, the inner shaft including a substantially rectangular shaped proximal end; and an actuating member comprising a handle, a leg member extending therefrom, and a stopping shoulder extending around the leg member, wherein the substantially rectangular shaped proximal end of the inner shaft is insertable into the leg member of the actuating member.

* * * * *